United States Patent [19]

Browner et al.

[11] Patent Number: 4,762,995

[45] **Date of Patent: * Aug. 9, 1988**

[54] MONODISPERSE AEROSOL GENERATOR

[75] Inventors: Richard F. Browner, Atlanta, Ga.; Ross C. Willoughby, Pittsburgh, Pa.

[73] Assignee: Georgia Tech Research Corporation, Atlanta, Ga.

[ * ] Notice: The portion of the term of this patent subsequent to Aug. 18, 2004 has been disclaimed.

[21] Appl. No.: 841,324

[22] Filed: Mar. 19, 1986

Related U.S. Application Data

[63] Continuation-in-part of Ser. No. 623,711, Jun. 22, 1984, Pat. No. 4,629,478.

[51] Int. Cl.[4] .......... B01D 59/44

[52] U.S. Cl. .......... 250/282; 250/288

[58] Field of Search .......... 250/282, 288, 281; 261/78 A

[56] References Cited

U.S. PATENT DOCUMENTS

| | | | |
|---|---|---|---|
| 2,887,181 | 5/1959 | Dillon | 261/78 A |
| 2,966,312 | 12/1960 | Wilson | 261/78 A |
| 3,421,692 | 1/1969 | Babington et al. | 261/78 A |
| 3,633,027 | 1/1972 | Ryhage | 250/288 |
| 3,997,298 | 12/1976 | McLafferty et al. | 73/61.1 C |
| 4,055,987 | 11/1977 | McFadden | 250/288 |
| 4,066,411 | 1/1978 | Fine et al. | 73/61.1 C |
| 4,112,297 | 9/1978 | Miyagi et al. | 250/288 |
| 4,209,696 | 6/1980 | Fite | 250/288 |
| 4,213,326 | 7/1980 | Brodasky | 250/288 |
| 4,268,460 | 5/1981 | Boiarski et al. | 261/78 A |
| 4,281,246 | 7/1981 | White et al. | 250/282 |
| 4,298,795 | 11/1981 | Takeuchi et al. | 250/288 |
| 4,300,044 | 11/1981 | Iribarne et al. | 250/288 |
| 4,391,778 | 7/1983 | Andresen et al. | 250/288 |
| 4,403,147 | 9/1983 | Melera et al. | 250/288 |
| 4,531,056 | 7/1985 | Labowsky et al. | 250/281 |

OTHER PUBLICATIONS

Berglund, R. N. and Liu, B. Y. H., Env. Sci. & Technology, 7, 147, (1973).
Lindblad, et al., J. Sci. Instrum., 42, 635, (1965).
Baldwin et al., F.W. Org. Mass. Spectrom., 7, 1353, (1973).
McFadden, W. H., J. Chromatogr. Sci., 18, 97, (1980).
McAdams, et al., 26th Annual Conference on Mass Spectrometry and Allied Topics, St. Louis, Mo., (1978).

*Primary Examiner*—Bruce C. Anderson

*Attorney, Agent, or Firm*—Newton, Hopkins & Ormsby

[57] ABSTRACT

A monodisperse aerosol generator forms a stable jet of liquid at a velocity allowing columnar breakup into droplets of uniform size and spacing. To prevent degradation of the monodisperse aerosol, it is dispersed by entrainment in a high velocity gaseous stream. To provide an interface for direct injection into a mass spectrometer or to interface a liquid chromatograph with a mass spectrometer, the generator is followed by a desolvation chamber operating at about atmospheric pressure and a multistage pressure reducer which evacuates solvent vapor and gaseous medium to form a high momentum, solvent-depleted solute aerosol beam which is input into the mass spectrometer. To permit the analysis of higher molecular weight molecules that may be either involatile or thermal sensitive, a fast atom bombardment (FAB) source is used for the production of FAB mass spectra.

7 Claims, 3 Drawing Sheets

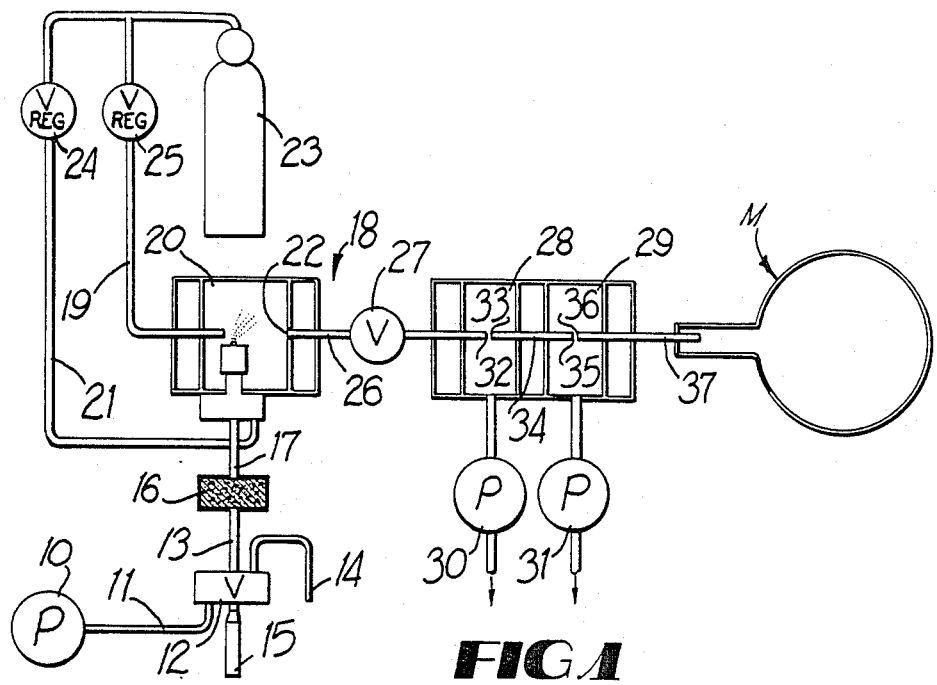
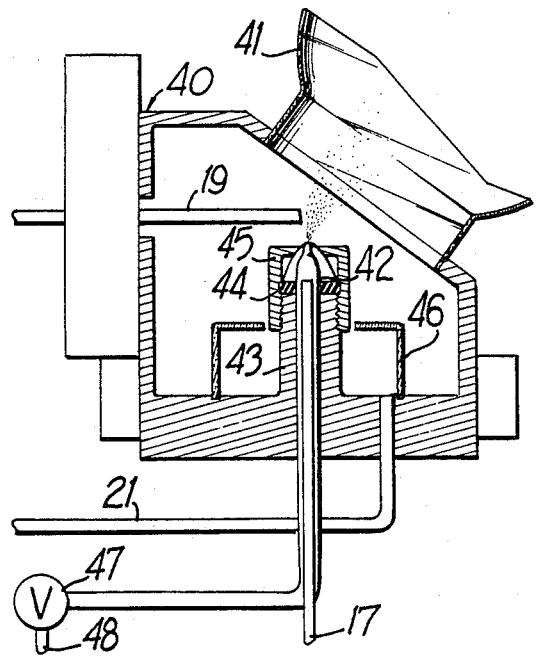
FIG 1
FIG 2

MONODISPERSE AEROSOL GENERATOR

This invention was made in part with Government support under Grant CHE-8019947 awarded by the National Science Foundation. The Government has certain rights in this invention.

This is a continuation-in-part of Application Ser. No. 623,711, filed June 22, 1984, now U.S. Pat. No. 4,629,478.

BACKGROUND OF THE INVENTION

This invention relates to a monodisperse aerosol generator and interface structure for forming an aerosol beam and introducing it into mass spectrometry apparatus. The monodisperse aerosol generator has separate utility aside and apart from the interface structure inasmuch as it may be used as a primary aerosol standard for reference purpose, as a source of injection of uniform particles to internal combustion devices, and as a source of sample solution introduction in flame and plasma atomic spectrometry (e.g., atomic absorption, atomic emission and atomic fluorescence spectroscopy). The monodisperse aerosol generator is, however, primarily intended for use as a means of solution introduction to a device acting as an interface between a liquid chromatograph and a mass spectrometer, or for direct introduction of sample solutions to the interface without the use of the liquid chromatograph. The preferred interface structure according to this invention accepts the monodisperse aerosol and desolvates it to form a solute aerosol beam which, with high purity, is introduced into a mass spectrometer.

The device is intended to provide a source of aerosol particles with a narrow particle size distribution, with a high degree of efficiency. It will be capable of producing aerosol from a wide range of liquids of varying physical properties. These liquids will include water and solutions of substances soluble in water, organic solvents and solutions of substances soluble in organic solvents. The device will produce a stable aerosol, such that the aerosol, once formed, will show little tendency to coagulate to form agglomerates of particles. The aerosol will, however, be capable of controlled evaporation for partial or complete removal of solvent. The size of the aerosol droplets will be controllable by simple means.

The device will be capable of producing a uniform and reproducible concentration of droplets in the gas stream over an extended period of time. It will also be capable of generating droplets with a wide range of selected sizes, covering a range typically of 5–200 micrometers in diameter. Liquid chromatography, particularly modern high performance liquid chromatography, provides a powerful tool for the separation of complex mixtures of either organic or inorganic species into their components. It is suitable for a great range of compounds which cannot be separated using the technique of gas chromatography. Such compounds may be thermally unstable or involatile under normal gas chromatographic conditions. Many organic compounds of biological significance, and most ionic and inorganic compounds fall in this category.

Mass spectrometry is a very widely used technique for providing structural information about chemical species. Often, an unknown species may be identified with great certainty, by comparison of its mass spectrum with that of a reference mass spectrum obtained from a species of known composition. For reliable mass spectral identification of unknown species, it is generally necessary for the mass spectrometer to fulfill the following requirements: (1) mass spectra should be generated by the electron or atomic impact mode of ionization; and (2) mass spectra should be generated from one species only at a time.

Many molecules, especially biological molecules of higher molecular weight cannot be analyzed by mass spectrometry using either electron or chemical ionization techniques. To overcome this limitation, a fast atom bombardment (FAB) source is attached to the mass spectrometer to provide a stream of fast atoms for the ionization of higher molecular weight compounds.

In a liquid chromatograph, a stream of solvent, containing a mixture of chemical species in solution, is passed at elevated pressure through a chromatographic column. The column is so designed that it separates the mixture, by differential retention on the column, into its component species. The different species then emerge from the column as distinct bands in the solvent stream, separated in time. The liquid chromatograph provides, therefore, an ideal device for the introduction into a mass spectrometer of single species, separated from initially complex mixtures.

In order for the species emerging from the column to be introduced into a mass spectrometer, partial or total removal of solvent from the dissolved species is desirable. This serves the following purposes: (1) it allows the ionization chamber of the mass spectrometer to operate at normal operating pressures (e.g., $10^{-5}$ to $10^{-6}$ torr for electron impact ionization; 1 torr for chemical ionization; $10^{-5}$ torr torr for atomic impact ionization); and (2) it allows normal ionization modes, such as electron or atomic impact, chemical or other to be used. Without efficient solvent removal from the species entering the ionization chamber of the mass spectrometer, hybrid and less well characterized mass spectra are produced. These types of mass spectra are generally of diminished value for unknown compound identification.

One purpose of the invention is to provide a means of introducing small samples of substances, dissolved in suitable solvent, directly into a mass spectrometer for either electron or atomic impact mass spectrometry. The interface must remove the solvent and its vapor to a sufficiently low level that either impact mode of operation may be used. The interface may be used either as a rapid means of directly introducing samples into a mass spectrometer, or as an interface between a liquid chromatograph and a mass spectrometer. It is intended that the interface should take advantage of the inherent capabilities of each component technique, without compromising either.

Specifically, preferred goals of the invention are: (1) to allow direct, simple interfacing between the liquid chromatograph and the mass spectrometer; (2) to provide efficient species transport between the liquid chromatograph and the mass spectrometer; (3) to allow the use of all normal modes of ionization typically used for gas chromatograph/mass spectrometry; (4) to allow operation with a wide variety of solvents (this would include solvents and solvent mixtures commonly used in normal, reversed phase and ion exchange liquid chromatography, e.g., alcohols, nitriles, and aqueous buffers, together with mixtures of same); (5) to produce sufficiently high species enrichment in the liquid chromatography effluent, by solvent removal, that the desolvated species may be introduced directly to the ionization chamber of a normal mass spectrometer, without need for additional high pumping capacity in the mass spectrometer; (6) to allow the device to be readily incorporated into the ionization chambers of existing instruments, with minimum modification (e.g., through the direct probe inlet); (7) to be capable of reliable, routine operation; (8) to be capable of providing precise, quantitative analysis of species over at least two orders of magnitude mass range.

Previous methods for generating uniform aerosols directly from liquid streams have worked on the principle of applying a regular external disturbance to a liquid cylindrical jet. The disturbance has been applied either axially or longitudinally to the jet as it emerges from a uniform circular nozzle. The disturbance has been provided by an electromechanical device, such as a piezoelectric crystal or a loudspeaker coil, driven by a high frequency power source.

The orifices used have either been laser-drilled steel or platinum disks, or fine bore stainless steel or glass capillary tubes. In general, the smallest droplets claimed for the devices are approximately 10 micrometers for circular disk orifices and 40 micrometers for capillary devices. A typical disk device is that of Berglund and Liu.[1] The liquid is passed under pressure through a disk orifice, emerging as a jet which is periodically disturbed by oscillations from a piezoelectric crystal. The piezoelectric crystal is driven at a selected frequency by a radiofrequency generator. Stable and uniform aerosol production is only possible over a restricted range of liquid flow and oscillating frequency, for each particular orifice size. The initial aerosol stream is dispersed by a concentric gas jet, diluted with further air and neutralized electrically with a radioactive source, before emerging from the device.
[1] Berglund, R. N. and Liu, B.Y.H. Env. Sci & Technology, 7,147 (1973).

Capillary devices are typified by that of Lindblad and Schneider.[2] Here liquid emerges from a stainless capillary tube, is subjected to transverse disturbances from a piezoelectric crystal under radiofrequency oscillations, and breaks into a uniform droplet stream. In general, the droplet density produced by the capillary type devices is lower than that produced by the disk devices, and so dilution gas for prevention of agglomeration is not used.
[2] Lindblad, N. R. & Schneider, J. M., J.Sci. Instrum., 42,635 (1965).

Other devices typically used for aerosol production, and suitable for use with a wide range of solvents and solutions are pneumatic nebulizers and spinning disk nebulizers. Devices are also available which are based on ultrasonic aerosol production using focussed-beam devices.

A number of approaches to interfacing liquid chromatography with mass spectrometry have been attempted. They may be summarized under the following categories:

Direct Liquid Introduction (DLI). With this approach, the interface between the liquid chromatograph and the mass spectrometer consists of a direct probe, having a stainless steel diaphragm at the tip. The center of the diaphragm has a small (typically 1-10 micrometer) orifice, through which part of the column effluent is sampled into the ionization chamber of the mass spectrometer, through a desolvation chamber. A liquid stream emerges from the orifice, and shatters into droplets. The droplets pass into a desolvation chamber, which is cryogenically cooled in order to trap solvent vapor, and maintain a reasonable operating pressure in the ionization chamber. The system was first described by Baldwin and McLafferty,[3] and is marketed commercially by Hewlett-Packard and Ribermag. Versions have been described for both normal [1] and microcolumn [2] liquid chromatography.
[3] Baldwin, M. A. & McLafferty, F. W. Org. Mass. Spectrom. 7,1353 (1973).

Mechanical Transfer Techniques. With mechanical transfer techniques, all of part of the effluent is collected onto a moving wire or belt. The liquid either flows directly onto the wire or belt, or is sprayed on as an aerosol. In either instance, a thin film of the liquid is formed, from which the solvent is evaporated in stages. The belt (or wire) passes through several independently pumped chambers, separated by vacuum locks, before reaching the ionization chamber of the mass spectrometer. In the first chamber, the belt is usually heated radiantly, in order to evaporate solvent from the column effluent. Prior to the ion source, the belt is heated rapidly, in order to flash vaporize the species from the belt, and allow it to pass into the ion source chamber. A typical system of this type is that of McFadden,[4] which is available commercially from Finnigan Instruments. Another version (available commercially from (VG-Organic) passes the belt directly up into the ionization chamber, in order to allow surface ionization techniques to be used.
[4] McFadden, W. H., J. Chromatogr. Sci. 18, 97 (1980).

Aerosol Introduction Techniques. These derivatives of the DLI approach attempt to produce more efficient evaporation of solvent from the liquid chromatography column effluent, prior to its entering the ionization chamber of the mass spectrometer. The effluent emerges as a liquid jet from a small orifice, which is heated to a high temperature (typically 1000° C., using an oxyhydrogen flame). The partly desolvated aerosol particles are separated from the solvent vapor by means of a skimmer, before passing to the ionization chamber of the mass spectrometer. Such a device has been described by McAdams et al.,[5] and is available commercially from Finnigan Instruments.
[5] McAdams, M. J., Blakley, C. R. and Vestal, M. L., 26th Annual Conference on Mass Spectrometry and Allied Topics, St. Louis, Mo. (1978).

In addition to the above, the following patents as submitted in copending U.S. Pat. application Ser. No. 775,035 are noted in that they relate generally to interface structure for use in a combined liquid chromatography - mass spectrometry system:

U.S. Pat. No. 4,055,987; McFadden; 11/01/77
U.S. Pat. No. 4,066,411; Fine et al.; 01/03/78
U.S. Pat. No. 4,112,297; Miyagi et al.; 09/05/78
U.S. Pat. No. 4,281,246; White et al.; 07/28/81
U.S. Pat. No. 4,298,795; Takeuchi; 11/03/81
U.S. Pat. No. 4,300,044; Iribarne et al.; 11/10/81
U.S. Pat. No. 4,403,147; Melera et al.; 09/06/83
U.S. Pat. No. 3,633,027; Rykage; 01/04/72
U.S. Pat. No. 3,997,298; McLafferty et al.; 12/14/76
U.S. Pat. No. 4,213,326; Brodasky; 07/22/80
U.S. Pat. No. 5 4,391,778; Andresen et al.; 07/05/83

No relevant prior art is known with relation to the monodisperse aerosol generator per se.

BRIEF DESCRIPTION OF THE DRAWING FIGURES

FIG. 1 is a schematic view of the invention in use as an interface;

FIG. 2 is a sectional view through a monodisperse aerosol generator according to the invention;

Figure 3:
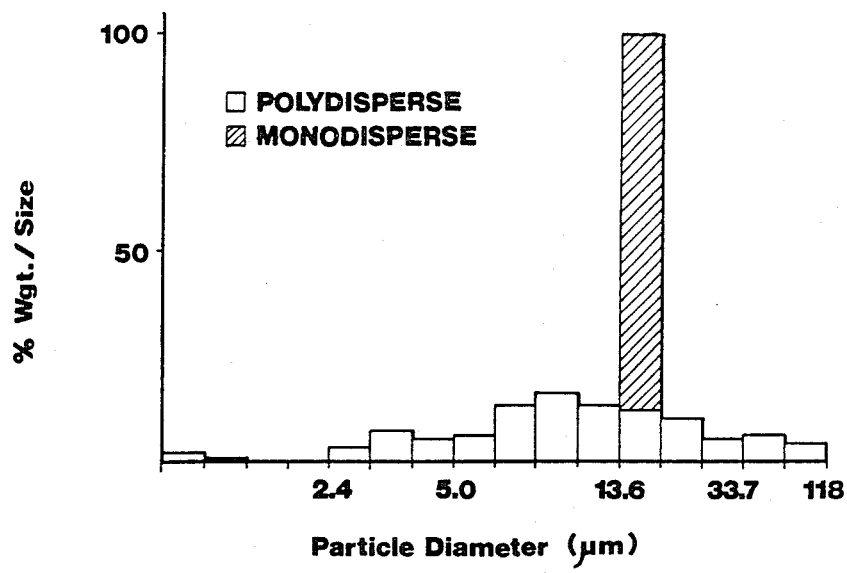

FIG. 2 illustrates the nebulizer or monodisperse aerosol generator according to this invention. As shown, the housing 40 is provided, having a glass ball joint 41 for connection to the desolvation chamber (FIG. 1), for containing the nebulizer. The nebulizer structure in FIG. 2 comprises the glass tip 42 seated in the top of the body 43 through the intermediary of a suitable sealing gasket or O-ring 44 and held in place by the cap 45 threaded onto the body 43 as shown. Immediately below the cap 45 is the sheath gas distributing housing 46 to which the line 21 is connected and the body 43 has a central passage leading to the split flow control valve 47 having the outlet 48. The solution is pumped through the line 17 previously described and causes same to issue as a stable jet from the tip of the nozzle 42.

Figure 4:
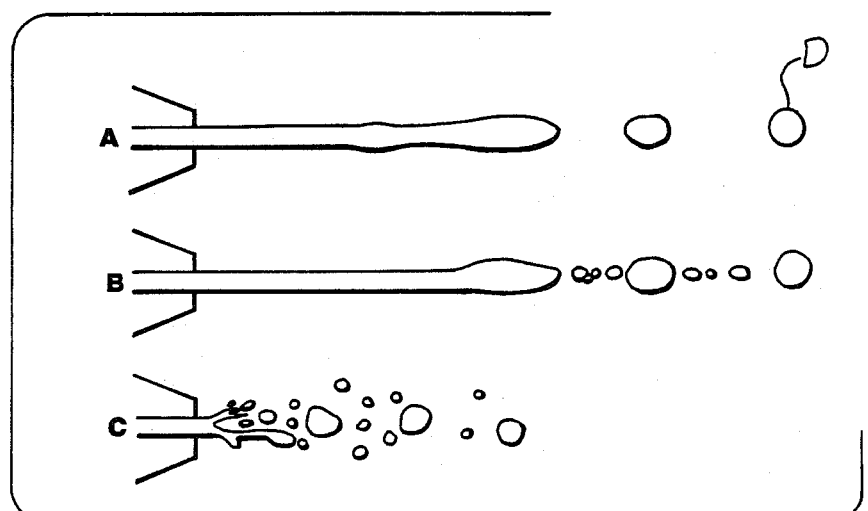

Although the diameter of the nozzle orifice may range between about 2 to about 100 micrometers, the range of about 9 to about 20 micrometers is preferred for nozzle 42. The stable jet is controlled as to its velocity so that it is subjected to the columnar breakup as indicated in FIG. 4 at A. Progressively higher velocities are depicted at B and C which respectively illustrate sinuous breakup and atomization.

The columnar or monodisperse breakup of A is Rayleigh breakup and produces droplets or particles D of substantially uniform size and spacing, the droplet diameters being about two times the orifice diameter. Generally speaking, with the preferred orifice diameters, the stable jets with Rayleigh breakup were produced with flow rates below about 1 mL/min.

The glass nebulizer tip in FIG. 2 is constructed from thick-walled glass capillary tubing of approximately 0.25 inches external diameter. One end of the tube is initially flame sealed, to give a conical closure to the tube. This end is then opened, by grinding with a fine abrasive medium (such as 400 grade silicon carbide paper), until an orifice of suitable diameter has been created. The diameter of the orifice may be measured using a calibrated microscope. The other end of the tube is formed into a lip, which is ground on its lower edge to form a liquid-tight seal against the gasket placed in the threaded end of the metal block. The nebulizer tip is held in place with the retaining cap.

Figure 6:
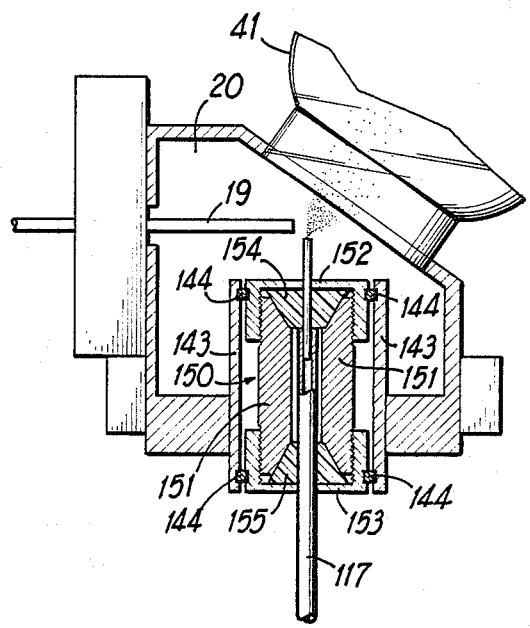

FIG. 6 illustrates an alternate embodiment of the monodisperse aerosol generator wherein the nebulizer tip is a cylindrical capillary tube 142 which is seated in sample line 117. Capillary tube 142 may be constructed of metal, glass, silica or any other suitable sturdy material capable of being manufactured to the appropriate size of approximately 25 micrometers internal diameter. Capillary tube 142 extends downwardly into sample line 117 for a distance of about 4 mm and is secured in place by compression fitting 150.

Compression fittings are commercially available from several manufacturers. The compression fitting 150, illustrated in FIG. 6, is made by Valco and comprises essentially a central externally threaded cylinder 151, which is fitted with internally threaded upper and lower caps 152 and 153, respectively. Upper ferrule 154 and lower ferrule 155 are constructed of a high temperature plastic and are deformable to the extent that, as upper cap 152 and lower cap 153 are screwed into place onto cylinder 151, upper ferrule 154 compresses tightly against capillary tube 142 and lower ferrule 155 compresses tightly against the sample line 117. Upper ferrule 154 also functions as a seal because sample line 117 has an internal diameter of approximately 250 micrometers, which is considerably larger than the external diameter of capillary tube 142. Body 143 is adapted to provide a tight seal with compression fitting 150 by the placement of a set of O rings 144 between body 143 and upper and lower caps, 152 and 153.

Figure 5:
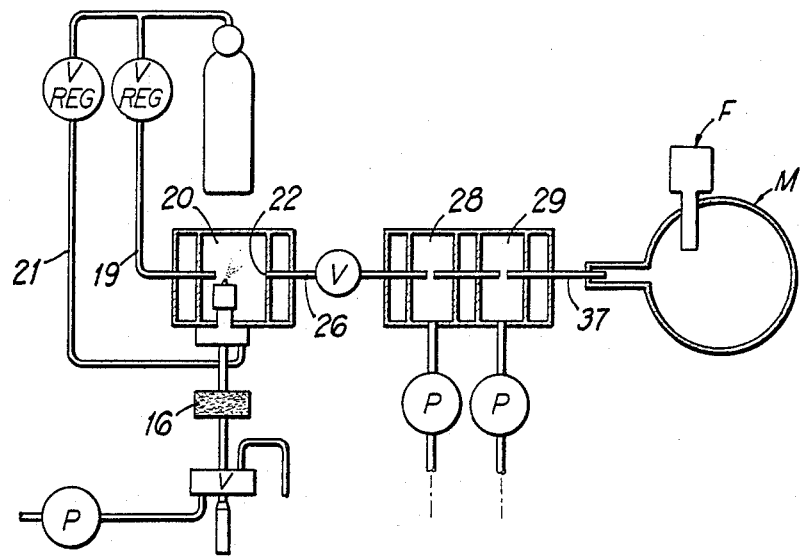

The capillary tube nozzle tip 142, as illustrated in FIG. 6, has a preferred orifice diameter of approximately 25 micrometers, which is slightly larger than that of the conical nozzle tip 42 illustrated in FIG. 2. Several advantages are derived by incorporating the nozzle tip 142, as shown in FIG. 6, into the aerosol generating device. For example, the in-line filter system 16, illustrated in FIG. 1, can be eliminated because capillary nozzle tip 142 is not as prone to blockage as conical tip 42. Also, the improved sample flow eliminates the need for a sheath gas and a split flow outlet. Therefore, the construction of the generator can be simplified by eliminating sheath gas line 21, sheath gas housing 46, split flow control valve 47, and outlet 48. The dispersion gas entering through line 19 has been found to be sufficient for the desolation step and to maintain the chamber space 20 substantially at atmospheric pressure. Line 19 dispersion gas is also sufficient to carry the aerosol droplets to outlet orifice 22 and through outlet tube 26 into evacuation chambers 28 and 29 (FIGS. 1 and 5).

The liquid supply to both embodiments comes from a pump, capable of sustaining liquid flows in the range of 0.01 to 1.0 mL/min., at pressures up to approximately 300 pounds per square inch. The pump should also provide little pressure pulsation in operation. A typical pump used is one suitable for High Performance Liquid Chromatography.

Dispersion gas is introduced from a capillary tube, constructed from stainless steel or some other suitable rigid material. The dispersion gas tube is positioned with suitable alignment devices, to be fixed at between 3 and 10 mm above the tip of the glass orifice. Dispersion gas, controlled by suitable means such as pressure controllers, needle valves, and rotameters, flows through the dispersion gas capillary at a flow adequate to produce efficient dispersion of the aerosol. Flows will typically be in the range of 0.5 to 2.0 L/min. of gas.

The aerosol produced by the device may be sampled by any appropriate means, or pass into a desolvation chamber or sampling port of another device by sealing the aerosol generation device into a closed chamber. This first chamber may then be sealed to subsequent devices, to ensure efficient transfer of the aerosol to these devices.

FIG. 5 shows the monodisperse aerosol generator with FAB source F attached to mass spectrometer M. The generation of FAB spectra also requires that the sample be present in pure form. Small micrometer particles, free of solvent matrix are ideal for the production of FAB mass spectra.

The primary differences between this device and previous devices, and the advantages resulting from these, are the following:

(1) No source of external mechanical distrubance is needed for the operation of the device.

(2) The orifice may be either capillary tubing or readily constructed therefrom, to produce highly circular openings of 2 micrometers diameter and above.

(3) The diameter of the aerosol produced by the device is controlled by the diameter of the liquid orifice. The aerosol particle diameter is approximately $2.1 \times$ the orifice diameter. The precise relationship between aero- FIG. 3 is a graph comparing monodisperse and polydisperse aerosols as referred to herein;

FIG. 4 illustrates columnar breakup (A) according to this invention in comparison to sinuous breakup (B) and atomization (C);

FIG. 5 is a schematic view of the invention in use as an interface showing a fast atom bombardment source.

FIG. 6 is a sectional view through a monodisperse aerosol generator according to an alternate embodiment of the invention showing a capillary tube nozzle tip.

DETAILED DESCRIPTION OF THE INVENTION

FIG. 1 illustrates that form of the invention forming an interface for use in a combined liquid chromatography-mass spectrometry system or for direct injection into the mass spectrometer. The relatively pulseless pump 10 of the liquid chromatograph system pumps effluent eluted from the chromatograph column (not shown) into the line 11 in which an optional six port sample valve 12 may be interposed. In the combined system, sample injection is not used but provision may be necessary to reduce the flow through the outlet line 13 and, for this purpose, split flow may be adjusted with part of the effluent being directed over the line to waste or to suitable collection means. For direct injection, the pump 10 may pump only solvent in the line 11 and the sample may be introduced as by the syringe 15.

In any event, the solution is filtered at 16 before passing through the line 17 to the monodisperse aerosol generator 18. Although "monodisperse" implies a single aerosol droplet or particle size, that term is used herein to mean droplets or particles which have a very narrow range of sizes. The meaning should be clear from FIG. 3 wherein typical monodisperse aerosol within the meaning therein is compared with a polydisperse aerosol. The polydisperse aerosol illustrated in FIG. 3 was generated from a PerkinElmer crossed flow pneumatic nebulizer whereas the monodisperse aerosol was generated according to this invention using a 6 um orifice, as will be described presently. The measurements from which FIG. 3 was generated were of Fraunhofer diffraction from the aerosols generated.

As will be explained more fully hereinafter, the monodisperse aerosol is entrained in a high velocity gas jet emanating from the capillary 19 and is directed into the confined space 20 for the purpose of desolvation. The aerosol is suitably diluted with sheath gas entering from the line 21 in amount sufficient to maintain the desolvation chamber space 20 substantially at atmospheric pressure. The use of substantially atmospheric pressure in the chamber 20 greatly enhances the desolvation process and allows the monodisperse aerosol droplets or particles to the substantially completely depleted of the solvent so that by the time the aerosol reaches the outlet orifice 22 it is in the form of solvent-depleted solute.

The dispersion and sheath gases preferably are inert such as argon or helium from a suitable supply 23. Their rates of flow over the line 21 and to the capillary 19 may be adjusted by the respective flow regulators 24 and 25.

The chamber 20 may typically be 40 mm in diameter and approximately 30 cm long. The outlet tube 26 may be a ½ inch stainless steel tube provided with a suitable shut-off valve 27 to isolate the relatively high pressure chamber 20 from the vacuum region.

The vacuum region is shown as comprised of the two chambers 28 and 29 connected to the respective pump

30 and 31. Typically the pump 30 evacuates the chamber at a rate of about 300 liters per minute to maintain the chamber 28 at a pressure in the range of 2–10 torr whereas the pump 31 typically evacuates about 150 liters per minute to maintain the chamber 29 at a pressure in the range 0.1 to 1 torr.

The nozzle end 32 of the tube 26 is precisely aligned with the flat end 33 of the tube 34 forming the first skimmer. The separation between 33 and 34 typically may be about 1–3 cm. Similarly, the separation between the nozzle end 35 and the flat end 36 of the outlet tube 37 may be in the 1–3 cm range.

With the internal diameter of the nozzle 32 being 0.5 mm whereas the internal diameters of the two skimmers 33 and 36 and also of the nozzle 35 being 1.0 mm optimum results were obtained as were also obtained by using 0.5 mm inside diameters for all but the skimmer 33 whose inside diameter was 1.0 mm.

Operation of the System

1. Direct injection mode. In this mode of operation, a constant flow of solvent is supplied to the monodisperse aerosol generator 18 with the low-pulse liquid pump 10. The monodisperse generator produces a finely dispersed solvent aerosol which passes, together with the dispersion gas, into the desolvation chamber 20. In the desolvation chamber, the majority of the solvent evaporates. The combination of dispersion gas and solvent vapor then passes sequentially through the two pressure reduction chambers 28, 29 where the mixture of dispersion gas and solvent vapor is removed by the vacuum pumps 30, 31.

Samples are introduced to the system by means of an injector 15. The sample may be either a pure liquid, or consist of a solution of solid or liquid in a suitable solvent. The injector may be either a multi-port valve, a septum injection system, or a high performance liquid chromatography auto-injector system. Generally, a small sample volume (typically 5–100 microliters), is introduced, which might typically contain a few micrograms or nanograms of the substance to be analyzed. The aerosol generated by the monodisperse generator now passes through the desolvation chamber and the two pressure reduction chambers, as with the pure solvent stream. However, when sample is present in the solvent stream, a highly dispersed aerosol of sample material remains after solvent evaporation. This aerosol finally enters the ionization chamber of the mass spectrometer M, where ions are generated for subsequent mass analysis. Separation of aerosol and gas/vapor mixture is effective because the desolvated aerosol particles gain sufficient momentum in their transit through the skimmers of the interface so that they are largely unaffected by the pumping in the vacuum chambers.

2. HPLC coupled mode. Operation of the interface with a high performance liquid chomatograph is very similar to operation with the direct injection device described in the previous section. The only substantial difference is that the sample may now contain a mixture of compounds, which are separated into individual compounds by passage through a chromatography column. The chromatography column is placed between the injector valve and the aerosol generator. Mass spectrometers can generally only analyze one compound at a time and so the separation of complex mixtures into individual compounds is a pre-requisite for normal mass spectrometric analysis.

sol diameter and orifice diameter is dependent on the compressibility of the liquid.

(4) The selection of aerosol diameter, by interchange of orifices, may be accomplished readily and rapidly.

(5) The device operates very stably over extended periods of time without the need for adjustment.

(6) The device operates very reproducibly from day to day, without the need for realignment of components, or the re-optimization of parameters, between runs.

(7) A wide variety of liquids may be used with the device, requiring only that the contents of the liquid reservoir be changed in order to change the liquid to be converted to an aerosol. Both water, organic solvents, mixtures of water and organic solvents, and mixtures of organic solvents may be used with the device.

(8) Inorganic and organic species may be dissolved in any of the solvents or solvent mixtures mentioned in item (7) at concentrations up to 1% by weight of dissolved solids, without blockage problems occurring in the device.

(9) The FAB source permits atomic impact ionization of high molecular weight compounds for the generation of mass spectra. The combination of electron impact spectra for the low molecular weight compounds, together with the FAB spectra for the higher molecular weight compounds, provides the mass spectroscopist with the ability to analyze the entire range of compounds likely to be of interest.

It will be appreciated that to prevent degradation of the monodisperse aerosol generation due to coagulation and/or impact between droplets, the dispersion must be effected near the point of random or Rayleigh breakup, by dispersing the aerosol at an angle, preferably about 90°, to the axis of the stable jet. It will also be appreciated that the vacuum means continuously evacuates gaseous medium solvent vapor and solvent-depleted solute, while separating off the solvent vapor and gaseous medium to form the monodisperse aerosol beam of solvent-depleted solute. This beam has high momentum and passes through the final skimmer into the ion source. It should also be understood that the solvent-depleted solute beam consists of particles of smaller size than those of the originally generated aerosol and contains a somewhat greater relative size range of distribution.

It should also be noted that this invention serves two very distinct purposes: (1) as a novel source of monodispersed particles, which would have potential applications in the area of aerosol calibration and particle generation, and (2) the interface between a flowing liquid stream and a low pressure mass spectrometer. Although the interface contains the aerosol generator, the combination of physical processes to remove solvent from the droplets and enrich the solute particles is also critical for the performance of the interface.

What is claimed is:

1. A method of introducing solute recovered from effluent of a liquid chromatograph into a mass spectrometer, which comprises the steps of:

(a) generating a monodisperse aerosol from the effluent by delivering the effluent through a conduit at a velocity such that monodisperse droplet formation occurs
    (b) providing a dispersing gas;
    (c) dispersing the formed droplets with the gas;
    (d) entraining the aerosol in gas and desolvating the aerosol at substantially atmospheric pressure;
    (e) expanding the components of step (b) (d) into low pressure environment while removing gas therefrom to form a high momentum monodisperse aerosol beam of solute particles;
    (f) directing said beam into a mass spectrometer; and
    (g) ionizing the monodisperse beam of solute particles by bombarding the solute particles with atoms originating from a fast atom bombardment source.

2. A system for introducing solvent depleted solute recovered from effluent of a liquid chromatograph into a mass spectrometer which comprises:

(a) means for generating a monodisperse aerosol from the effluent by supplying liquid to a nozzle at a rate sufficient to produce a stable jet of liquid having a velocity such that monodisperse droplet breakup of the jet occurs;
    (b) dispersing means for entraining the droplets just after the point of droplet formation in a high velocity flow of gas so as to retain the monodisperse nature thereof;
    (c) a desolvating chamber for producing the solvent depleted solute;
    (d) pressure reduction means for expanding said gas with entrained droplets into a low pressure environment while removing gas therefrom to form a high momentum monodisperse aerosol beam of solute particles;
    (e) means for directing said beam into a mass spectrometer; and
    (f) a fast atom bombardment source for ionizing the monodisperse beam by bombarding the solute particles with atoms originating therefrom.

3. The method of claim 1 wherein said gas removal comprises the step of:

expanding said aerosol and gas into a first vacuum chamber having a pressure in the range of 2-10 torr.

4. The method of claim 3 wherein said gas removal further comprises the step of:

expanding said aerosol and gas from said first vacuum chamber to a second vacuum chamber having a pressure in the range of 0.1 to 1.0 torr.

5. The system of claim 2 wherein said desolvating chamber is maintained at about atmospheric pressure.

6. The system of claim 2 further comprising a vacuum chamber for continuously evacuating gaseous medium and a vacuum pump which maintains said vacuum chamber at a pressure in the range of 2-10 torr.

7. The system of claim 6 further comprising a second vacuum chamber and a second vacuum pump which maintains said second vacuum chamber at a pressure in the range of 0.1-1.0 torr.

* * * * *